United States Patent
Yamada et al.

(10) Patent No.: US 8,673,329 B2
(45) Date of Patent: Mar. 18, 2014

(54) OIL-IN-WATER-TYPE EMULSION COSMETIC

(75) Inventors: Kenichi Yamada, Odawara (JP); Hideki Kodashima, Odawara (JP); Takashi Fukui, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/508,392

(22) PCT Filed: Nov. 4, 2010

(86) PCT No.: PCT/JP2010/069633
§ 371 (c)(1),
(2), (4) Date: May 7, 2012

(87) PCT Pub. No.: WO2011/055761
PCT Pub. Date: May 12, 2011

(65) Prior Publication Data
US 2012/0251603 A1    Oct. 4, 2012

(30) Foreign Application Priority Data

Nov. 6, 2009 (JP) ................. 2009-255092
Nov. 25, 2009 (JP) ................. 2009-267092

(51) Int. Cl.
*A61K 8/06* (2006.01)
*A61Q 17/04* (2006.01)
*A61K 8/81* (2006.01)

(52) U.S. Cl.
USPC ........................ 424/401; 514/938

(58) Field of Classification Search
USPC ........................ 424/401; 514/938
See application file for complete search history.

(56) References Cited

U.S. PATENT DOCUMENTS

| | | | | |
|---|---|---|---|---|
| 5,093,099 | A | * | 3/1992 | Haishi et al. .............. 423/622 |
| 7,172,754 | B1 | * | 2/2007 | Rosevear et al. .............. 424/59 |
| 2005/0228056 | A1 | * | 10/2005 | Asai et al. .............. 516/53 |
| 2012/0219608 | A1 | * | 8/2012 | Yamada et al. .............. 424/401 |

FOREIGN PATENT DOCUMENTS

| | | |
|---|---|---|
| CN | 1488666 A | 4/2004 |
| JP | 01 175921 | 7/1989 |
| JP | 7 173044 | 7/1995 |
| JP | 8 12526 | 1/1996 |
| JP | 9 137152 | 5/1997 |
| JP | 3073887 | 8/2000 |
| JP | 2000-297005 | 10/2000 |
| JP | 2003 104859 | 4/2003 |
| JP | 2005 272389 | 10/2005 |
| JP | 2006 8796 | 1/2006 |
| JP | 2007 326902 | 12/2007 |
| JP | 2008 44901 | 2/2008 |
| JP | 4245831 | 4/2009 |

OTHER PUBLICATIONS

U.S. Appl. No. 13/480,570, filed May 25, 2012, Fukui, et al.
U.S. Appl. No. 13/480,581, filed May 25, 2012, Fukui, et al.
International Search Report Issued Feb. 8, 2011 in PCT/JP10/69633 Filed Nov. 4, 2010.

* cited by examiner

*Primary Examiner* — Lezah Roberts
*Assistant Examiner* — Tracy Liu
(74) *Attorney, Agent, or Firm* — Oblon, Spivak, McClelland, Maier & Neustadt, L.L.P.

(57) ABSTRACT

Provided is an oil-in-water emulsified cosmetic composition having a high UV-protective effect and also having an excellent long-term stability and an excellent feeling upon application. The oil-in-water emulsified cosmetic composition is characterized by containing a zinc oxide powder (A) having an average particle diameter of 0.1 to 1 μm, an average particle thickness of 0.01 to 0.2 μm, and an average aspect ratio of 3 or more and a polymer (B) selected from the group consisting of a polyacrylamide compound, a polyacrylic acid, and salts thereof.

14 Claims, No Drawings

OIL-IN-WATER-TYPE EMULSION COSMETIC

CROSS REFERENCE TO RELATED APPLICATION

This application is a 371 of PCT/JP10/069633, filed on Nov. 4, 2010, and claims priority to the following Japanese Patent Applications: 2009-255092, filed on Nov. 6, 2009; and 2009-267092, filed on Nov. 25, 2009.

FIELD OF THE INVENTION

The present invention relates to an oil-in-water emulsified cosmetic composition having an excellent UV-protective effect, excellent long-term stability, and an excellent feeling upon application.

BACKGROUND OF THE INVENTION

Recently, it has been pointed out that ultraviolet ray in the UV-A region (320 to 400 nm) penetrates deep into the skin, becoming the main causative factor for photoaging and skin cancer. In view of this, the demand has also risen for cosmetics with a UV-protective effect in the UV-A region.

Conventionally, ultraviolet absorbers such as 2-ethylhexyl paramethoxycinnamate and inorganic powders such as titanium dioxide and zinc oxide have been used for protection against ultraviolet ray. Among them, zinc oxide has recently been frequently used in cosmetics for its relatively high shielding ability against not only the UV-B region (290 nm to 320 nm) but also the UV-A region.

However, when zinc oxide was used in an oil-in-water emulsified cosmetic composition, a problem arises that it was difficult to be blended into the cosmetic composition owing to its poor dispersibility in an aqueous system. Also, even when zinc oxide was used in combination with water-soluble polymers to increase the dispersion stability, a problem arises that zinc ions dissolved from zinc oxide caused aggregation of the water-soluble polymers, dramatically reducing long-term stability and feeling upon application of the cosmetic composition.

As a solution to the aforementioned problems, for example, there has been proposed an oil-in-water emulsified cosmetic composition having favorable powder dispersibility and long-term stability and an excellent feeling upon application obtained by using a copolymer of acryloyldimethyl taurate and hydroxyethyl acrylate and a powder such as titanium dioxide (refer to Patent Document 1). However, a problem thereof is that unless a specific acrylic silicone is used in combination as a dispersant in the oil-in-water emulsified cosmetic composition, the powder dispersibility becomes poor, and the acrylic silicone adversely produces a tight skin feeling, impairing the feeling upon application.

Also, there has been proposed an oil-in-water emulsified cosmetic composition having favorable long-term stability and excellent feeling upon application, transparency, and water resistance obtained by using zinc oxide, a cross-linking copolymer of acrylamide and 2-acrylamido-2-methylpropanesulfonic acid and/or an acrylic acid-sodium acryloyldimethyl taurate copolymer, a surfactant having an HLB of 10 or more, silicone oil, and water (refer to Patent Document 2). However, it has insufficient transparent feeling when applied and also poor spreadability, and thus is not satisfactory in terms of usability.

Meanwhile, there has been proposed a skin external agent having improved transparency and UV-protective effect obtained by using a flaky powder of zinc oxide (refer to Patent Document 3).

PRIOR ART DOCUMENTS

Patent Document

[Patent Document 1] JP-A-2006-8796
[Patent Document 2] JP-A-2005-272389
[Patent Document 3] JP-B-3073887

SUMMARY OF THE INVENTION

The present invention is an oil-in-water emulsified cosmetic composition containing a zinc oxide powder (A) having an average particle diameter of 0.1 to 1 µm, an average particle thickness of 0.01 to 0.2 µm, and an average aspect ratio of 3 or more and a polymer (B) selected from the group consisting of a polyacrylamide compound, a polyacrylic acid, and salts thereof.

Effects of the Invention

The oil-in-water emulsified cosmetic composition of the present invention has a high UV-protective effect and excellent long-term stability. Further, it also has smoothness upon application and excellent transparent feeling upon application, providing a favorable feeling upon application.

EMBODIMENTS FOR CARRYING OUT THE INVENTION

However, even when the aforementioned powder is used, the powder dispersibility remains insufficient and the cosmetic composition is still unsatisfactory in terms of unnaturally white spots resulting from blending of this powder and the feeling upon application.

Accordingly, an object of the present invention is to provide an oil-in-water emulsified cosmetic composition having a high UV-protective effect and excellent long-term stability and feeling upon application.

Under the foregoing circumstances, the present inventors conducted intensive research in order to achieve the aforementioned object. As a result, they have found that when a zinc oxide powder having an average particle diameter of 0.1 to 1 µm, an average particle thickness of 0.01 to 0.2 µm, and an average aspect ratio of 3 or more is used in combination with an acrylamide compound in an oil-in-water emulsified cosmetic composition, the resulting cosmetic composition can achieve not only a high UV-protective effect but also excellent long-term stability and feeling upon application, thereby completing the present invention.

Hereinbelow, the configuration of the present invention will be described in detail.

Examples of the zinc oxide powder (A) having an average particle diameter of 0.1 to 1 µm, an average particle thickness of 0.01 to 0.2 µm, and an average aspect ratio of 3 or more (hereinbelow, referred to as a flaky powder of zinc oxide) used in the present invention include flaky powder of zinc oxide described in JP-A-1-175921, JP-A-1-230431, JP-A-8-12526 and JP-A-9-137152, for example.

Here, the arithmetic average of the major axis and the minor axis of arbitrary 20 particles present in an arbitrary visual field in a transmission electron micrograph was regarded as the average particle diameter. The average particle thickness was obtained by the arithmetic mean of measured thickness of all of the particles having a measurable thickness in the visual field in the transmission electron micrograph. The average aspect ratio was obtained by (the average particle diameter)/(the average particle thickness), and the resulting value was rounded off to the nearest whole number.

As to the form of the flaky powder of zinc oxide (A) used in the present invention, the average particle diameter is 0.1 to 1 μm, preferably 0.1 to 0.8 μm, and more preferably 0.2 to 0.7 μm. When the average particle diameter is less than 0.1 μm, the flaky powder of zinc oxide aggregates, resulting in reduced dispersibility, while when it exceeds 1 μm, the transparency and the protective capacity against ultraviolet ray are reduced.

The average particle thickness is 0.01 to 0.2 μm, preferably 0.01 to 0.1 μm, and more preferably 0.01 to 0.05 μm. When the average particle thickness is less than 0.01 μm, the flake form is prone to crumble, while when it exceeds 0.2 μm, the flaky powder of zinc oxide will cause a feeling of discomfort when blended into the cosmetic composition. Thus, an average particle thickness of less than 0.01 μm or more than 0.2 μm is impractical.

The average aspect ratio is 3 or more, preferably 5 or more, and more preferably 7 or more. Also, the upper limit of the average aspect ratio is preferably 30 or less. When the average aspect ratio is less than 3, the transparency is reduced.

The flaky powder of zinc oxide (A) used in the present invention preferably further contains a trace element having a valence of +2 or more. Here, the term "contain" means that the trace element is bound to, or retained in, the surface or inside of the flaky powder of zinc oxide.

Examples of the trace element having a valence of +2 or more include metals such as iron, zirconium, calcium, manganese, magnesium, and yttrium. These trace elements may be used alone or a combination of two or more of them may be used, and examples of the combination include zirconium and iron, zirconium and magnesium, iron and magnesium, and iron and calcium. From the viewpoint of the protective capacity against ultraviolet ray, the content of the trace element is preferably 0.005 to 1.0 mole, more preferably 0.01 to 0.5 mole per 100 moles of zinc contained in the flaky powder of zinc oxide (A).

Here, the content of the element added was obtained by dissolving a predetermined amount of dry powder in 6 N hydrochloric acid, diluting the resulting solution to a predetermined volume, and analyzing it by inductively coupled plasma (ICP) atomic emission spectrometry to obtain the concentrations of zinc and other elements added, and then calculating the mole ratio of the element added to zinc.

The flaky powder of zinc oxide (A) used in the present invention is contained in an amount of preferably 0.5 to 20% by weight, particularly preferably 1 to 18% by weight of the total amount of the oil-in-water emulsified cosmetic composition. When the amount of the flaky powder of zinc oxide (A) is within the above range, good powder dispersibility is obtained and also an increase in the viscosity of the preparation can be prevented.

The polymer (B) used in the present invention is one or two or more polymers selected from the group consisting of a polyacrylamide compound, a polyacrylic acid, and salts thereof. Examples of the polyacrylamide compound include a polyacrylamide copolymer and an acrylamide copolymer. Examples of the polyacrylamide copolymer include a copolymer having acrylamide and/or acryloyldimethyl taurate as a constituent unit. Also, examples of the polyacrylic acid or a salt thereof include polyacrylic acid and sodium polyacrylate.

As the sodium polyacrylate, for example, RM2051 Thickening Agent (sodium polyacrylate, dimethicone, cyclopentasiloxane, trideceth-6, and PEG/PPG-18/18 dimethicone), which is a complex material supplied by Dow Corning Toray Co., Ltd., and the like may be used.

Examples of the polyacrylamide and its copolymer include a hydroxyethyl acrylate/sodium acryloyldimethyl taurate copolymer, a sodium acrylate/acryloyldimethyl taurate copolymer, polyacrylamide, sodium polyacrylate, and an acrylamide/ammonium acrylate copolymer.

As the hydroxyethyl acrylate/sodium acryloyldimethyl taurate copolymer, for example, SEPINOV EMT 10, or SIMULGEL NS which is a complex material (a hydroxyethyl acrylate/sodium acryloyldimethyl taurate copolymer, squalane, polysorbate 60, and water; 35 to 40% by weight of the hydroxyethyl acrylate/sodium acryloyldimethyl taurate copolymer is contained), both of which are supplied by SEPPIC, may be used.

As the sodium acrylate/acryloyldimethyl taurate copolymer, for example, SIMULGEL EG (a sodium acrylate/acryloyldimethyl taurate copolymer, isohexadecane, polysorbate 80, and water; 37.5% by weight of the sodium acrylate/acryloyldimethyl taurate copolymer is contained), SIMULGEL EPG (a sodium acrylate/acryloyldimethyl taurate copolymer, polyisobutene, (caprylyl/capryl) glucoside, and water), both of which are complex materials supplied by SEPPIC, and the like may be used.

Examples of the polyacrylamide include a cross-linked copolymer of 2-acrylamido-2-methylpropanesulfonic acid, and for example, SEPIGEL 305 (polyacrylamide, hydrogenated polyisobutene, laureth-7, and water; 40% by weight of polyacrylamide is contained) and SEPIGEL 501 (polyacrylamide, polysorbate 85, mineral oil, and isoparaffin; 20% by weight of polyacrylamide is contained), both of which are complex materials supplied by SEPPIC, may be used.

As the acrylamide/ammonium acrylate copolymer, SEPIPLUS 265 (an acrylamide/ammonium acrylate copolymer, polyisobutene, polysorbate 20, and water), which is a complex material supplied by SEPPIC, and the like may be used.

Among these, the polymer (B) is preferably polyacrylamide or an acrylamide copolymer, more preferably a hydroxyethyl acrylate/sodium acryloyldimethyl taurate copolymer, a sodium acrylate/acryloyldimethyl taurate copolymer, and polyacrylamide. When these polymers are used, the resulting cosmetic compositions are insusceptible to be affected by eluted ions, while attaining excellent long-term stability.

In the present invention, the content of the polymer (B) is preferably 0.1 to 5% by weight, more preferably 0.2 to 4% by weight of the total amount of the oil-in-water emulsified cosmetic composition. When the content of the polymer (B) is within the above range, a favorable feeling upon application and excellent long-term stability are achieved.

In addition to the aforementioned flaky powder of zinc oxide (A), a metal oxide powder (C) having an average particle diameter of 0.01 to 1 μm and an average aspect ratio of less than 3 (hereinbelow, referred to as a fine particle metal oxide powder) may be used in the oil-in-water emulsified cosmetic composition of the present invention. From the standpoint of a high UV-scattering effect, the fine particle metal oxide powder is preferably one or two or more selected from the group consisting of zinc oxide, titanium dioxide, and cerium oxide.

Also, as in the flaky powder of zinc oxide (A), the fine particle metal oxide powder may contain a trace element having a valence of +2 or more, and the aforementioned fine particle metal oxide powder may contain metals such as iron, zirconium, calcium, manganese, magnesium, and yttrium singly or as an appropriate combination of two or more of them.

The fine particle zinc oxide powder (C) is commercially available as, for example, FINEX-25, FINEX-50, and FINEX-75 (manufactured by Sakai Chemical Industry Co., Ltd.), MZ500 series, MZ700 series (manufactured by Tayca Corporation), and ZnO-350 (manufactured by Sumitomo Osaka Cement Co., Ltd.). The fine particle titanium dioxide powder is commercially available as, for example, TTO-55 series, TTO-51 series (Ishihara Sangyo Kaisha, Ltd.), JR series, and JA series (Tayca Corporation). Also, examples of the fine particle cerium oxide include high-purity cerium sold by Nikki Co., Ltd. or AGC Seimi Chemical Co., Ltd. Among them, the fine particle metal oxide powder (C) is particularly preferably a fine particle zinc oxide powder or a fine particle titanium dioxide powder.

Examples of the form of the fine particle metal oxide powder (C) used in the present invention include a spherical form, a rod-like form, a spindle-like form, a needle-like form, and an indeterminate form; however, as long as the average particle diameter is within the aforementioned range, the fine particle metal oxide powder in any form may be used. Also, the fine particle metal oxide powder has an average aspect ratio of preferably 2 or less, more preferably 1.5 or less. When the average aspect ratio is within the above range, high transparency and a favorable UV-protective effect are achieved even when it is used in combination with the flaky powder of zinc oxide (A).

The average particle diameter of the fine particle metal oxide powder (C) used in the present invention is within a range of preferably 0.01 to 1 μm, more preferably 0.012 to 0.2 μm, and even more preferably 0.015 to 0.1 μm. When the above average particle diameter is less than 0.01 μm, the powder becomes highly active and has strong aggregability, and this causes, in many cases, such a powder to substantially behave as a powder having a particle diameter equal to or larger than the applicable range of the present invention as a secondary particle. Also, when the average particle diameter exceeds 1 μm, there may be an optical problem such as the opacification tendency of the preparation.

The fine particle metal oxide powder (C) used in the present invention is contained in an amount of preferably 0.5 to 20% by weight, more preferably 1 to 18% by weight of the total amount of the oil-in-water emulsified cosmetic composition. When the content of the fine particle metal oxide powder (C) is within the above range, favorable powder dispersibility is achieved and a problem of a large increase in the viscosity of the preparation is avoided.

The flaky powder of zinc oxide (A) and/or the fine particle metal oxide powder (C) are preferably subjected to various types of surface treatment such as fluorine compound treatment, silicone treatment, silicone resin treatment, pendant treatment, silane coupling agent treatment, titanate coupling agent treatment, oil agent treatment, N-acylated lysine treatment, polyacrylic acid treatment, metallic soap treatment, amino acid treatment, inorganic compound treatment, plasma treatment, mechanochemical treatment, treatment using a silane or silazane compound, in advance.

Preferable examples include treatment using methyl hydrogen polysiloxane or the methyl hydrogen polysiloxane-dimethylpolysiloxane copolymer represented by the following formula (1) as a surface treatment agent and treatment using a silane or silazane compound as a surface treatment agent. Of these, surface treatment using a silane or silazane compound as a surface treatment agent is more preferred.

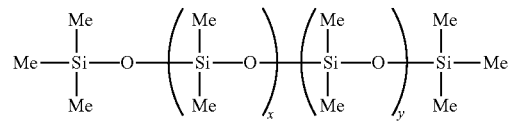

wherein, x and y are each an integer and $1 \leq x+y \leq 60$.

As the aforementioned silane or silazane compound, a silane or silazane compound having a $C_{1-20}$ alkyl or fluoroalkyl group and having reactivity with an inorganic oxide is preferred, which is specifically shown as the silane compound represented by the following formula (2) or the silazane compound represented by the following formula (3). One or more of these silane or silazane compounds may be used.

wherein, n is an integer of 0 or 1, R represents a $C_{1-20}$ alkyl or fluoroalkyl group (which may be linear or branched), $R^1$ represents a $C_{1-6}$ alkyl group, and X represents a halogen atom or an alkoxy group, and

wherein, $R^2$ to $R^7$ may be the same or different and each represent a $C_{1-20}$ alkyl or fluoroalkyl group (which may be linear or branched).

Specific examples of the silane compound include hexyltrimethoxysilane, octyltrimethoxysilane, decyltrimethoxysilane, octadecyltrimethoxysilane, octyltriethoxysilane, trifluoropropyltrimethoxysilane, and heptadecafluorodecyltrimethoxysilane. Among them, octyltriethoxysilane and octyltrimethoxysilane are preferable. Preferred examples of a silazane compound include hexamethyldisilazane and octyldisilazane, of which octyldisilazane is more preferable. The aforementioned silane or silazane compounds are preferable because they have such characteristics that they can easily be treated uniformly and are easily supplied, and are inexpensive in terms of cost, and further, when a flaky powder of zinc oxide (A) and/or a fine particle metal oxide powder (C) having been subjected to surface treatment with these compounds are blended into products, excellent characteristics such as dispersibility are obtained.

Examples of the treatment method with the aforementioned silane or silazane compound include a method including allowing a silane or silazane compound to undergo chemical reactions with a reactive group on the surface of a metal oxide such as a zinc oxide in a method such as a method including mixing a silane or silazane compound and a metal oxide such as a zinc oxide powder in an organic solvent such as n-hexane, cyclohexane, and a lower alcohol, and performing pulverization, if necessarily, and then removing the organic solvent by heating or reducing pressure, and applying heat treatment preferably at 80 to 250° C.

Examples thereof also include a method which includes subjecting a cosmetic pigment to coating treatment with a specific polysiloxane compound, and then to surface treatment using alkylalkoxysilane in water as described in JP-A-2007-326902.

The amount of the surface treatment agent for coating the flaky powder of zinc oxide (A) and/or the fine particle metal oxide powder (C) is preferably 3 to 15% by weight, more preferably 5 to 10% by weight of the total amount of these powders used. When the amount of the coating is within the above range, the surface of these powders is uniformly coated with the surface treatment agent and the surface treatment agent is prevented from aggregating or precipitating on the surface of the powder of a zinc oxide or the like.

In the present invention, the total amount of the flaky powder of zinc oxide (A) and the fine particle metal oxide powder (C) is preferably 1 to 35% by weight, more preferably 2 to 25% by weight of the total amount of the oil-in-water emulsified cosmetic composition. When the total amount of (A) and (C) is within the above range, an excellent feeling upon application and favorable long-term stability are achieved.

In the present invention, the blending ratio (weight ratio) of the flaky powder of zinc oxide (A) to the fine particle metal oxide powder (C), (A)/(C), is preferably 1/5 to 10/1, more preferably 1/5 to 5/1, and even more preferably 2/5 to 5/2. When the blending ratio is within the above range, not only high transparency and UV-protective effect but also excellent long-term stability and a smooth feel upon application are achieved.

In the oil-in-water emulsified cosmetic composition of the present invention, an ester (D) of a $C_{12-22}$ linear fatty acid and a $C_{6-24}$ linear or branched alcohol may further be used. Specific examples thereof include hexyl laurate, myristyl myristate, cetyl myristate, cetyl palmitate, stearyl stearate, decyl oleate, oleyl oleate, cetyl ricinoleate, isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, and octyldodecyl ricinoleate. One or two or more of these esters can be used.

Among them, a preferred ester is an ester of a $C_{14-18}$ linear fatty acid and a $C_{8-20}$ branched alcohol, and specific examples thereof include isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, and octyldodecyl ricinoleate.

The content of the ester (D) used in the present invention is preferably 0.5 to 10% by weight, more preferably 1 to 5% by weight of the total amount of the oil-in-water emulsified cosmetic composition. It is preferable that the content of the ester (D) be within the above range since the oily feeling is reduced, while smooth spreadability is obtained.

A polysaccharide (E) may further be used in the oil-in-water emulsified cosmetic composition of the present invention. The polysaccharide in the present invention is one which produces a monosaccharide of at least ten molecules by hydrolysis. Specifically, examples of the polysaccharide include pullulan, dextran, cyclosophoran, laminarin, schizophyllan, lentinan, arabinogalactan, barley glucan, lichenan, succinoglycan, xyloglucan, locust bean gum, xanthan gum, chitosan, pustulan, carrageenan, hyaluronic acid, or a salt thereof, among which xanthan gum, carrageenan, hyaluronic acid, or a salt thereof are preferred.

Xanthan gum is a β-linked polysaccharide produced when the bacteria belonging to *Xanthomonas* (*Xanthomonas campestris*) are cultivated in pure culture in a glucose or starch medium. It is a light yellow powder having a molecular weight of ten million or more. It is commercially available as NOMCORT (manufactured by The Nisshin OilliO Group, Ltd.) and ECHO GUM (manufactured by Dainippon Sumitomo Pharma Co., Ltd.).

Carrageenan is a polysaccharide having a sulfate group obtained by alkaline extraction of raw algae in the family Gigartinaceae of Rhodophyceae. It is commercially available as NEOMOIST MT (manufactured by Maruzen Pharmaceuticals Co., Ltd.) and CP Gum FA (manufactured by Dainippon Sumitomo Pharma Co., Ltd.).

Hyaluronic acid or a salt thereof is a high-viscosity mucopolysaccharide obtained by extraction from the chicken comb or by a fermentation method using modified *Streptococcus Zooepidemicus* or *Streptococcus equi*, which is a species of *Lactococcus*. It is commercially available as hyaluronic acid FCH series (manufactured by Kikkoman Biochemifa Company) and hyaluronic acid liquid HA series (manufactured by Kewpie Corporation). Specific examples of the salt thereof include a sodium salt and a potassium salt.

In the present invention, the content of the polysaccharide is preferably 0.0001 to 5% by weight, more preferably 0.05 to 3% by weight of the total amount of the oil-in-water emulsified cosmetic composition. The content of the polysaccharide (E) within the above range is preferable because when it is used with the flake-like zinc oxide and the like, the resulting emulsified cosmetic composition is free from sticky feeling while having good long-term stability.

In order to further improve the protective capacity against ultraviolet ray, the oil-in-water emulsified cosmetic composition of the present invention may contain an organic ultraviolet absorber. Examples of the organic ultraviolet absorber used in the present invention include 2-hydroxy-4-methoxybenzophenone, 2-hydroxy-4-methoxybenzophenone-5-sulfonic acid, 2,2'-dihydroxy-4,4'-dimethoxybenzophenone, disodium 2,2'-dihydroxy-4,4'-dimethoxy-5,5'-disulfobenzophenone, 2,4-dihydroxybenzophenone, 2,2',4,4'-tetrahydroxybenzophenone, 4-tert-butyl-4'-methoxy-dibenzoylmethane, 2,4,6-trianilino-p-(carbo-2'-ethylhexyl-P-oxy)-1,3,5-triazine, menthyl anthranilate, 2-(2-hydroxy-5-methylphenyl)benzotriazole, and 2-(4-diethylamino-2-hydroxybenzoyl)-hexyl benzoate.

Among the aforementioned organic ultraviolet absorbers, when 2-(4-diethylamino-2-hydroxybenzoyl)-hexyl benzoate is blended into the oil-in-water emulsified cosmetic composition of the present invention, the resulting emulsified cosmetic composition can achieve a particularly excellent UV-protective effect and a good feeling upon application without a sticky feeling. This 2-(4-diethylamino-2-hydroxybenzoyl)-hexyl benzoate is an organic ultraviolet absorber represented by the following formula (4), and is commercially available as Uvinul A Plus (manufactured by BASF Japan, Ltd.). It absorbs ultraviolet ray within a range of 310 to 390 nm (UV-A region) with a maximum absorption wavelength of approximately 354 nm.

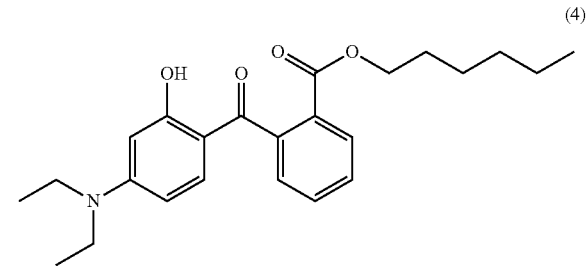 [SMILES: CCCCCCOC(=O)c1ccccc1C(=O)c1ccc(N(CC)CC)cc1O]

(4)

In the present invention, the content of the organic ultraviolet absorber is preferably 0.01 to 20% by weight, more preferably 0.05 to 10% by weight of the total amount of the oil-in-water emulsified cosmetic composition. When the content of the organic ultraviolet absorber is within the above range, an excellent UV-protective effect and good long-term stability are achieved.

Of the content of the organic ultraviolet absorber, the content of 2-(4-diethylamino-2-hydroxybenzoyl)-hexyl benzoate is preferably 0.01 to 8% by weight, more preferably 0.05 to 3% by weight of the total amount of the oil-in-water emulsified cosmetic composition.

Also, in the present invention, a polymer powder having the aforementioned organic ultraviolet absorber enclosed therein may be used. The polymer powder may or may not be hollow, and the average particle diameter may range from 0.1 to 50 and the particle size distribution may be broad or sharp. Examples of the kind of the polymer include acrylic resin, methacrylic resin, styrene resin, urethane resin, polyethylene, polypropylene, polyethylene terephthalate, silicone resin, nylon, and acrylamide resin. Among these polymer powders, a powder containing organic ultraviolet absorber in an amount of 0.1 to 30% by weight of the powder weight is preferable.

It is preferred that the content of a surfactant having an HLB of 10 or more be less than 1% by weight, preferably less than 0.5% by weight, and more preferably less than 0.4% by weight of the total amount of the oil-in-water emulsified cosmetic composition because long-term stability, water resistance, and the feeling upon application of the oil-in-water emulsified cosmetic composition of the present invention are sometimes deteriorated due to inclusion of a large amount of a surfactant having an HLB of 10 or more.

The oil-in-water emulsified cosmetic composition of the present invention may contain in addition to the above-described ingredients, as long as the effect of the present invention is not impaired, ingredients which are normally blended into cosmetic compositions such as various types of surfactants, oily ingredients, higher alcohols, lower alcohols, resin, thickening agents, anti-microbial preservatives, fragrances, humectants, salts, solvents, antioxidants, chelating agents, neutralizers, pH adjusters, insect repellents, and physiologically active ingredients.

The oil-in-water emulsified cosmetic composition of the present invention may be used as a cosmetic without any particular limitation; however, it is preferably used as a hair cosmetic composition such as a shampoo, a rinse-off conditioner, and other types of conditioners, and a skin cosmetic composition such as a facial wash, a cleansing cosmetic composition, a sunscreen cosmetic composition, a facial pack, and a massage cosmetic composition. Among them, it is more preferably applied to a sunscreen cosmetic composition, a suntan, a makeup base cosmetic composition, a foundation having a protective capacity against ultraviolet ray, and the like.

The formulation of the oil-in-water emulsified cosmetic composition of the present invention may be prepared as a liquid, an emulsion, a cream, a paste, a solid, a multilayered form, and the like. It may also be prepared as a sheet, a spray and a mousse.

EXAMPLES

Hereinbelow, the present invention will be described in more detail with reference to Examples; however, the present invention will not be limited by these Examples.

Before describing Examples, the production method of the powder used in the following Examples will be described.

Production Example 1

Production of Flake-Like Zinc Oxide

Into 315 ml of an aqueous solution containing $5 \times 10^{-2}$ mole of sulfuric acid, $1.6 \times 10^{-1}$ mole of zinc sulfate, $3.8 \times 10^{-2}$ mole of sodium sulfate, and, as a salt of a trace element, $1.6 \times 10^{-4}$ mole of ferrous sulfate were dissolved. Subsequently, while stirring the resulting solution at 6000 r.p.m. with a homo-mixer, 230 mL of a 2 N aqueous solution of sodium hydroxide was added over 15 seconds (pH=12.8) to allow precipitate to form, and stirring was continued for 10 minutes. The resulting solution was then matured at 100° C. for 90 minutes, filtered, washed with water, and dried at 230° C. for approximately 10 hours to give an ultraviolet absorptive powder. The thus-obtained powder was observed under a scanning electron microscope and confirmed to be a flake-like particle (with an average particle diameter of 0.25 μm, an average particle thickness of 0.019 μm, an aspect ratio of 13, and a content of iron element of 0.11 mol %).

Production Example 2

Production of a Flaky Powder of Zinc Oxide Subjected to Surface Treatment with Alkylsilane A slurry composed of 93 parts by weight of the flaky powder of zinc oxide produced in Production Example 1, 7 parts by weight of octyltriethoxysilane, and toluene was produced, which was then pulverized and crushed using a bead mill (DYNO-MILL, manufactured by Shinmaru Enterprises Corporation). Subsequently, toluene was distilled off by heating under reduced pressure, and the resulting product was subjected to heat treatment at 150° C. for 4 hours using an air blast stream-type dryer to give an octyltriethoxysilane-treated flaky powder of zinc oxide.

Production Example 3

Production of a Flaky Powder of Zinc Oxide Subjected to Surface Treatment with Silicone A slurry composed of 93 parts by weight of the flaky powder of zinc oxide produced in Production Example 1, 7 parts by weight of methyl hydrogen polysiloxane (KF-99P, manufactured by Shin-Etsu Chemical Co., Ltd.), and isopropyl alcohol was produced, which was thoroughly stirred and then pulverized. The solvent was distilled off by heating under reduced pressure, and the resulting product was subjected to heat treatment at 150° C. for 4 hours in the air to give a flaky powder of zinc oxide subjected to surface treatment with methyl hydrogen polysiloxane.

Production Example 4

Production of a Fine Particle Zinc Oxide Powder Subjected to Surface Treatment with Alkylsilane A slurry composed of 93 parts by weight of a fine particle zinc oxide powder (substantially spherical, an average particle diameter of 0.02 μm), 7 parts by weight of octyltriethoxysilane, and toluene was produced, which was then pulverized and crushed using a bead mill (DYNO-MILL, manufactured by Shinmaru Enterprises Corporation). Subsequently, toluene was distilled off by heating under reduced pressure, and the resulting product was subjected to heat treatment at 150° C. for 4 hours using an air blast stream-type dryer to give an octyltriethoxysilane-treated fine particle zinc oxide powder.

Production Example 5

Production of a Fine Particle Zinc Oxide Powder Subjected to Surface Treatment with Silicone A slurry composed of 95 parts by weight of a fine particle zinc oxide powder (substantially spherical, an average particle diameter of 0.02 μm), 5 parts by weight of methyl hydrogen polysiloxane (KF-99P, manufactured by Shin-Etsu Chemical Co., Ltd.), and isopropyl alcohol was produced, which was thoroughly stirred and then pulverized. The solvent was distilled off by heating under reduced pressure, and the resulting product was subjected to heat treatment at 150° C. for 4 hours in the air to give a fine particle zinc oxide powder subjected to surface treatment with methyl hydrogen polysiloxane.

Production Example 6

Production of a Fine Particle Titanium Dioxide Powder Subjected to Surface Treatment with Silicone A slurry composed of 95 parts by weight of a fine particle titanium dioxide powder (substantially spherical, an average particle diameter of 0.017 μm) and 5 parts by weight of methyl hydrogen polysiloxane (KF-99P, manufactured by Shin-Etsu Chemical Co., Ltd.), and isopropyl alcohol was produced, which was thoroughly stirred and then pulverized. The solvent was distilled off by heating under reduced pressure, and the resulting product was subjected to heat treatment at 160° C. for 4 hours in the air to give a fine particle titanium dioxide powder subjected to surface treatment with methyl hydrogen polysiloxane.

Production Example 7

Production of a Pigment Subjected to Surface Treatment with Silicone

Except for using a pigment grade talc instead of the fine particle titanium dioxide powder used in Production Example 6, treatment was performed by the same production method, whereby a talc subjected to surface treatment with methyl hydrogen polysiloxane was obtained. Further, yellow iron oxide and black iron oxide were also treated in a similar fashion to give yellow iron oxide subjected to surface treatment with methyl hydrogen polysiloxane and black iron oxide subjected to surface treatment with methyl hydrogen polysiloxane, respectively.

Examples 1 to 12 and Comparative Examples 1 to 5

Oil-in-water emulsified cosmetic compositions having the blending compositions as shown in the following Table 1 were prepared by the following production method. The oil-in-water emulsified cosmetic compositions thus obtained were subjected to an evaluation test as described below. The evaluation results are shown in Table 1 altogether.
(Evaluation Method)
(1) UV-Protective Effect
The SPF values were measured using an SPF analyzer (manufactured by Optometices Optometrics) and are shown according to the following criteria.

[Evaluation Criteria for UVB-Protective Effect]
A: an SPF value of 40 or more
B: an SPF value of 30 or more and less than 40
C: an SPF value of 20 or more and less than 30
D: an SPF value of less than 20
[Evaluation Criteria for UVA-Protective Effect]
a: a T (UVA) of less than 20%
b: a T (UVA) of 20% or more and less than 25%
c: a T (UVA) of 25% or more Here, T (UVA) is defined by the following formula.

$$T(UVA)(\%) = \frac{\sum_{320}^{400} T_\lambda \times \Delta\lambda}{\sum_{320}^{400} \Delta\lambda}$$

$\begin{cases} T_\lambda: \text{Transmittance (\%) at a given wavelength } \lambda \\ \Delta\lambda: \text{Interval between measured wavelengths} \end{cases}$ (2) Feeling Upon Application
An expert panel of 10 people was assigned to each evaluation item (however, panelists may overlap depending on the item). They actually used the preparations and evaluated Examples 1 to 12 and Comparative Examples 1 to 5 for "presence of a transparent feeling after application" and "smoothness upon application" according to the following evaluation criteria. The evaluation results for feeling upon application are shown in Table 1 based on the total score of all the panelists.
[Evaluation Criteria of the Panelist]

| Evaluation criteria | score |
|---|---|
| Felt a high effect | 5 |
| Felt an effect | 4 |
| Felt a slight effect | 3 |
| Felt only a subtle effect | 2 |
| Felt no effect | 1 |

[Evaluation Result of the Feeling Upon Application]
A: a total score of 40 or more
B: a total score of 35 or more and less than 40
C: a total score of 25 or more and less than 35
D: a total score of less than 25
(3) Long-Term Stability
Each sample was stored in a constant temperature bath at 60° C. for one month. The condition after one month was observed and judged using the following judgment criteria.
[Judgment Criteria for Storage Stability]
A: No change
B: a slight change in viscosity was observed
C: an apparent change in viscosity was observed
D: separation was observed

TABLE 1

| | Component | Example 1 | 2 | 3 | 4 | 5 | 6 | 7 | 8 | 9 | 10 | 11 | 12 | Comparative Example 1 | 2 | 3 | 4 | 5 |
|---|---|---|---|---|---|---|---|---|---|---|---|---|---|---|---|---|---|---|
| 1 | (A) Alkylsilane-treated flaky zinc oxide powder (Production Example 2) | 15 | — | — | 15 | 15 | 15 | 15 | 15 | 10 | 10 | 10 | 6 | — | — | — | — | 15 |
| 2 | (A) Silicone-treated flaky zinc oxide powder (Production Example 3) | — | 15 | — | — | — | — | — | — | — | — | — | — | — | — | — | — | — |
| 3 | Flake-like zinc oxide (Production Example 1) | — | — | 15 | — | — | — | — | — | — | — | — | — | — | — | — | — | — |
| 4 | (C) Alkylsilane-treated fine particle zinc oxide powder (Production Example 4) | — | — | — | — | — | — | — | — | 5 | — | 10 | 10 | 15 | — | — | — | — |
| 5 | (C) Silicone-treated fine particle titanium dioxide powder (Production Example 6) | — | — | — | — | — | — | — | — | — | 5 | — | — | — | 15 | — | — | — |
| 6 | 2-Ethylhexyl paramethoxycinnamate | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 |
| 7 | Diethylamino hydroxybenzoyl hexyl benzoate (*1) | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| 7 | (D) Isocetyl myristate | 3 | 3 | 3 | 3 | 3 | 3 | 3 | 1 | 3 | 3 | 3 | 3 | 3 | 3 | 3 | 3 | 3 |
| 8 | (D) Isostearyl palmitate | — | — | — | — | 3 | — | — | 2 | — | — | — | — | — | — | — | — | — |
| 9 | Decamethylcyclopentasiloxane | 5 | 5 | 5 | 5 | 5 | 5 | 5 | 5 | 5 | 5 | 5 | 5 | 5 | 5 | 5 | 5 | 5 |
| 10 | Dimethylpolysiloxane | 3 | 3 | 3 | 5 | 5 | 5 | 5 | 3 | 3 | 3 | 3 | 3 | 3 | 3 | 3 | 3 | 3 |
| 11 | (B) SEPIGEL 501 (*2) | — | — | — | 3 | — | — | — | — | — | — | — | — | — | — | — | — | — |
| 12 | (B) SIMULGEL EG (*3) | — | — | — | — | 3 | 3 | — | — | — | — | — | — | — | — | — | — | — |
| 13 | (B) SIMULGEL NS (*4) | — | — | — | — | — | — | — | — | — | — | — | — | — | — | — | — | — |
| 14 | (B) Sodium polyacrylate | — | — | — | — | — | — | — | — | — | — | — | — | — | — | — | — | — |
| 15 | Acrylic acid-acrylic methacrylate copolymer | — | — | — | — | — | — | — | — | — | — | — | — | — | — | — | 0.4 | 0.4 |
| 16 | Carboxy vinyl polymer | — | — | — | — | — | — | — | — | — | — | — | — | — | — | — | — | — |
| 17 | Sodium hydroxide | — | — | — | — | — | — | — | — | — | — | — | — | — | — | — | 0.2 | 0.2 |
| 17 | Disodium edetate | 0.02 | 0.02 | 0.02 | 0.02 | 0.02 | 0.02 | 0.02 | 0.02 | 0.02 | 0.02 | 0.02 | 0.02 | 0.02 | 0.02 | 0.02 | 0.02 | 0.02 |
| 18 | (E) Xanthan gum | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| 19 | Purified water | Balance | Balance | Balance | Balance | Balance | Balance | Balance | Balance | Balance | Balance | Balance | Balance | Balance | Balance | Balance | Balance | Balance |
| 20 | Ethanol | 10 | 10 | 10 | 10 | 10 | 10 | 10 | 10 | 10 | 10 | 10 | 10 | 10 | 10 | 10 | 10 | 10 |
| 21 | Phenoxyethanol | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| 22 | Paraben | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| | (A)/(C) | — | — | — | — | — | — | — | — | 2 | 2 | 1 | 0.6 | — | — | — | — | — |
| | Content of surfactant (HLB of 10 or more) | 0.27 | 0.27 | 0.27 | 0.23 | 0.15 | 0.15 | 0.27 | 0.27 | 0.27 | 0.27 | 0.27 | 0.27 | 0.27 | 0.27 | 0.27 | 0.27 | 0.27 |
| | Evaluation | | | | | | | | | | | | | | | | | |
| | Feeling upon application (Smoothness upon application) | A | A | B | B | A | B | B | A | A | A | A | B | C | D | D | C | C |
| | (Transparent feeling after application) | B | C | C | A | A | B | B | B | A | A | A | A | B | C | D | D | D |
| | Long-term stability | A | A | C | A | B | B | A | A | A | B | A | A | B | A | D | D | D |
| | UVA-protective effect | a | a | b | a | a | a | a | a | a | a | a | a | c | c | c | c | c |
| | UVB-protective effect | A | A | B | A | B | B | A | A | A | A | A | A | C | C | D | D | D |

(*1): Uvinul A Plus (manufactured by BASF Japan, Ltd.)
(*2): Containing 40% by weight of polyacrylamide
(*3): Containing 37.5% by weight of a sodium acrylate/sodium acryloyldimethyl taurate copolymer
(*4): Containing 37.5% by weight of a hydroxyethyl acrylate/sodium acryloyldimethyl taurate copolymer (Production Method)
A: Components (1) to (10) are homogeneously mixed with a disperser and heated to 70° C.
B: Components (11) to (16) are homogeneously mixed while stirring at 70° C.
C: While stirring B, A is gradually added for preliminary emulsification.
D: C is cooled to 40° C., to which components (17) to (19) are gradually added. The resulting mixture is stirred and homogenously mixed with a homomixer, deaerated, and then cooled to give an oil-in-water emulsified cosmetic composition.

Examples 13 and 14 and Comparative Examples 6 and 7

Oil-in-water emulsified cosmetic compositions having the blending compositions as shown in the following Table 2 were prepared by the following production method. The oil-in-water emulsified cosmetic compositions thus obtained were evaluated for a feeling upon application (the absence of a sticky feeling and the presence of a moist feeling), long-term stability, and a UV-protective effect based on the aforementioned evaluation criteria. The evaluation results are shown in Table 2 altogether.

zinc oxide (A) and the polymer (B) has a high UV-protective ability and an excellent feeling upon application (smoothness upon application, transparent feeling after application, a sticky feeling, and a moist feeling) and favorable long-term stability.

Hereinbelow, Formulation Examples of the oil-in-water emulsified cosmetic composition of the present invention will be shown. All of the following emulsified cosmetic compositions have a high transparent feeling and a high UV-protective effect with excellent long-term stability and an excellent feeling upon application.

Formulation Example 1

Oil-in-Water Emulsified Foundation

| (Component) | (% by weight) |
| --- | --- |
| Alkylsilane-treated flaky zinc oxide powder (Production Example 2) | 10.0 |
| Silicone-treated fine particle zinc oxide powder (Production Example 5) | 5.0 |

TABLE 2

|  |  |  | Example | | Comparative Example | |
| --- | --- | --- | --- | --- | --- | --- |
|  |  |  | 13 | 14 | 6 | 7 |
| Component |  |  |  |  |  |  |
| 1 | (A) | Alkylsilane-treated flaky zinc oxide powder (Production Example 2) | 10 | 10 | — | — |
| 2 | (C) | Alkylsilane-treated fine particle zinc oxide powder (Production Example 4) | 5 | 5 | — | 15 |
| 3 |  | 2-Ethylhexyl paramethoxycinnamate | 7.5 | 7.5 | 7.5 | 7.5 |
| 4 |  | 2-(4-Diethylamino-2-hydroxybenzoyl)-hexyl benzoate (*1) | 0.5 | 0.5 | 0.5 | 0.5 |
| 5 | (D) | Isocetyl myristate | 3 | 3 | 3 | 3 |
| 6 |  | Decamethylcyclopentasiloxane | 5 | 5 | 5 | 5 |
| 7 |  | Dimethylpolysiloxane | 5 | 5 | 5 | 5 |
| 8 | (B) | SIMULGEL EG (*3) | 3 | 3 | 3 | 3 |
| 9 |  | Disodium edetate | 0.02 | 0.02 | 0.02 | 0.02 |
| 10 | (E) | Xanthan gum | — | 0.1 | 0.1 | 0.1 |
| 11 | (E) | Hyaluronic acid | 0.01 | 0.01 | — | — |
| 12 |  | Purified water | Balance | Balance | Balance | Balance |
| 13 |  | Ethanol | 10 | 10 | 10 | 10 |
| 14 |  | Phenoxyethanol | 0.05 | 0.05 | 0.05 | 0.05 |
| 15 |  | Paraben | 0.1 | 0.1 | 0.1 | 0.1 |
| Evaluation |  |  |  |  |  |  |
| Feeling upon application (absence of sticky feeling) |  |  | A | A | B | D |
| (moist feeling) |  |  | A | A | B | C |
| Long-term stability |  |  | B | A | B | B |
| UVA-protective effect |  |  | a | a | c | b |
| UVB-protective effect |  |  | A | A | D | B |

(Production Method)
A: Components (1) to (7) are dissolved by heating at 70° C. and homogeneously mixed.
B: Components (8) to (12) are homogeneously dissolved and mixed at 70° C.
C: While stirring B, A is gradually added for preliminary emulsification.
D: C is cooled to 40° C., to which components (13) to (15) are gradually added, followed by stirring. The resulting mixture is homogenously mixed with a homomixer, deaerated, and then cooled to give an emulsified cosmetic composition.

As is apparent from Tables 1 and 2, the oil-in-water emulsified cosmetic composition containing the flaky powder of -continued

| (Component) | (% by weight) |
| --- | --- |
| Silicone-treated fine particle titanium dioxide powder (Production Example 6) | 10.0 |
| Silicone-treated talc (Production Example 7) | 3.0 |
| Silicone-treated yellow iron oxide (Production Example 7) | 0.8 |
| Silicone-treated black iron oxide (Production Example 7) | 0.16 |
| Isohexadecane | 5.0 |
| Methyltrimethicone | 5.0 |
| Octyl paramethoxycinnamate | 5.0 |
| Diethylamino hydroxybenzoyl hexyl benzoate | 1.0 |
| PEG-60 hydrogenated castor oil | 2.0 |

-continued

| (Component) | (% by weight) |
|---|---|
| 1,3-Butylene glycol | 6.0 |
| SEPIGEL 501 | 3.0 |
| (Containing 20% by weight of polyacrylamide, manufactured by SEPPIC) | |
| Succinoglycan | 0.2 |
| Carboxymethyl cellulose | 0.3 |
| Ethanol | 5.0 |
| Purified water | Balance |

Formulation Example 2

Oil-in-Water Sunscreen Emulsified Cosmetic Composition

According to the components shown below and a routine method, an oil-in-water sunscreen cosmetic composition was prepared. The resulting oil-in-water sunscreen emulsion was excellent in UV-A protective effect, usability, long-term stability, and water resistance.

| (Component) | (% by weight) |
|---|---|
| Alkylsilane-treated flaky zinc oxide powder (Production Example 2) | 10.0 |
| Silicone-treated flaky zinc oxide powder (Production Example 3) | 10.0 |
| 2-Ethylhexyl paramethoxycinnamate | 4.0 |
| Diethylamino hydroxybenzoyl hexyl benzoate | 1.0 |
| Polymethylsilsesquioxane | 3.0 |
| Dimethylpolysiloxane | 5.0 |
| Octyldodecyl myristate | 5.0 |
| SIMULGEL EG | 3.0 |
| (Containing 37.5% by weight of sodium acrylate/acryloyldimethyl taurate copolymer, manufactured by SEPPIC) | |
| Glycerin | 3.0 |
| Trimethylsiloxysilicate | 0.5 |
| Ethanol | 0.5 |
| Phenoxyethanol | 0.5 |
| Trisodium edetate | 0.01 |
| Xanthan gum | 0.1 |
| Sodium hyaluronate | 0.1 |
| Purified water | Balance |

Also, the compositions of the fragrances used in the aforementioned Examples and Formulation Examples are shown in Table 3.

TABLE 3

| Fragrance formulation | |
|---|---|
| Component | ‰ by weight |
| Terpineol | 10.00 |
| Terpinyl acetate | 2.00 |
| Cepionate | 60.00 |
| Methyl dihydrojasmonate | 250.00 |
| Indole | 0.05 |
| 2-Methyl-3-(3,4-methylenedioxy-phenyl)-propanal | 3.00 |
| Hydroxycitronellal | 20.00 |
| Hydroxycitronellol | 10.00 |
| p-t-Butyl-α-methylhydrocinnamic aldehyde | 35.00 |
| 4-(4-Hydroxy-4-methyl-pentyl)-3-cyclohexen-1-carboxyaldehyde | 75.00 |
| 3-Methyl-5-phenylpentanol | 20.00 |
| Phenylethyl alcohol | 10.00 |
| α-Ionone | 10.00 |
| β-Ionone | 20.00 |

TABLE 3-continued

| Fragrance formulation | |
|---|---|
| Component | ‰ by weight |
| γ-Methylionone | 10.00 |
| Dihydro-β-ionone | 25.00 |
| Benzyl salicylate | 150.00 |
| cis-3-Hexenyl salicylate | 30.00 |
| Eugenol | 0.80 |
| Cinnamic alcohol | 5.00 |
| Cinnamic aldehyde | 0.50 |
| Guaiol acetate | 1.00 |
| Guaiol | 0.50 |
| Cedrenyl acetate | 5.00 |
| Cedryl methyl ketone | 30.00 |
| 6,7-Dihydro-1,1,2,3,3-pentamethyl-4(5H)-indan | 2.00 |
| Vetiver acetate | 10.00 |
| 3-Methyl-5-(2,3,3-trimethyl-3-cyclopenten-1-yl)-pentan-2-ol | 2.00 |
| 2-Ethyl-4-(2,3,3-trimethyl-3-cyclopenten-1-yl)-2-buten-1-ol | 0.80 |
| Isobornyl cyclohexanol | 35.00 |
| Heliotropin | 10.00 |
| Coumarin | 2.00 |
| Vanillin | 2.00 |
| Ethyl vanillin | 0.10 |
| Muscone | 0.50 |
| Ethylene brassylate | 42.00 |
| 4,6,6,7,8,8-Hexamethyl-1,3,4,6,7,8-hexahydrocyclopentabenzopyran | 60.00 |
| Cyclopentadecanolide | 20.00 |
| Ambrettolide | 1.00 |
| γ-Undecalactone | 0.40 |
| γ-Decalactone | 0.10 |
| 4-(4-Hydroxyphenyl)-2-butanone | 0.50 |
| Musk ketone | 0.10 |
| Skatole | 0.01 |
| cis-Jasmon | 0.05 |
| Phenylethyl acetate | 0.10 |
| Civetone | 0.20 |
| γ-Nonalactone | 0.05 |
| α-Santalol | 0.20 |
| β-Santalol | 0.20 |
| Eugenyl acetate | 0.10 |
| α-Hexyl cinnamic aldehyde | 20.00 |
| α-Damascone | 0.04 |
| β-Damascone | 0.02 |
| β-Damascenone | 0.01 |
| δ-Damascene | 0.01 |
| Rose absolute | 0.50 |
| Rose oil | 4.50 |
| Sandalwood oil | 2.00 |
| Labdanum absolute | 0.05 |
| Cistus absolute | 0.01 |
| Vetiver oil | 0.50 |
| Guaiac wood oil | 0.10 |
| Total | 1000.00 |

The invention claimed is:

1. An oil-in-water emulsified cosmetic composition comprising a zinc oxide powder (A) having an average particle diameter of 0.1 to 1 μm, an average particle thickness of 0.01 to 0.2 μm, and an average aspect ratio of 3 or more and a polymer (B) selected from the group consisting of a polyacrylamide compound, a polyacrylic acid, and salts thereof, wherein
   the component (A) is a powder subjected to surface treatment with a silane or silazane compound having a $C_{1-20}$ alkyl or fluoroalkyl group and having reactivity with an inorganic oxide.

2. The oil-in-water emulsified cosmetic composition according to claim 1, wherein the polymer (B) is one or more selected from the group consisting of a hydroxyethyl acrylate/sodium acryloyldimethyl taurate copolymer, a sodium acrylate/acryloyldimethyl taurate copolymer, and polyacrylamide.

3. The oil-in-water emulsified cosmetic composition according to claim 1, further comprising a metal oxide powder (C) having an average particle diameter of 0.01 to 1 μm and an average aspect ratio of less than 3, wherein a weight ratio of the component (A) to the component (C), (A)/(C), is 1/5 to 10/1.

4. The oil-in-water emulsified cosmetic composition according to claim 1, further comprising an ester (D) of a $C_{12-22}$ linear fatty acid and a $C_{6-24}$ linear or branched alcohol.

5. The oil-in-water emulsified cosmetic composition according to claim 4, wherein the ester (D) is one or more selected from the group consisting of hexyl laurate, myristyl myristate, cetyl myristate, cetyl palmitate, stearyl stearate, decyl oleate, oleyl oleate, cetyl ricinoleate, isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, and octyldodecyl ricinoleate.

6. The oil-in-water emulsified cosmetic composition according to claim 1, further comprising one or two or more polysaccharides (E) selected from the group consisting of pullulan, dextran, cyclosophoran, laminarin, schizophyllan, lentinan, arabinogalactan, barley glucan, lichenan, succinoglycan, xyloglucan, locust bean gum, xanthan gum, chitosan, pustulan, carrageenan, hyaluronic acid, and a salt thereof.

7. The oil-in-water emulsified cosmetic composition according to claim 6, wherein the polysaccharide (E) is hyaluronic acid, an alkali metal salt of hyaluronic acid, or xanthan gum.

8. The oil-in-water emulsified cosmetic composition according to claim 3, wherein (A)/(C) is 1/5 to 5/1.

9. The oil-in-water emulsified cosmetic composition according to claim 3, wherein (A)/(C) is 2/5 to 5/2.

10. The oil-in-water emulsified cosmetic composition according to claim 1, wherein the silane compound is present and has the following formula (2):

$$RR^1_nSiX_{3-n} \qquad (2)$$

wherein, n is an integer of 0 or 1, R represents a $C_{1-20}$ alkyl or fluoroalkyl group which may be linear or branched, $R^1$ represents a $C_{1-6}$ alkyl group, and X represents a halogen atom or an alkoxy group.

11. The oil-in-water emulsified cosmetic composition according to claim 1, wherein the silazane compound is present and has the following formula (3):

$$R^2R^3R^4SiNHSiR^5R^6R^7 \qquad (3)$$

wherein, $R^2$ to $R^7$ may be the same or different and each represent a $C_{1-20}$ alkyl or fluoroalkyl group which may be linear or branched.

12. The oil-in-water emulsified cosmetic composition according to claim 1, wherein the silane compound is present and is selected from the group consisting of hexyltrimethoxysilane, octyltrimethoxysilane, decyltrimethoxysilane, octadecyltrimethoxysilane, octyltriethoxysilane, trifluoropropyltrimethoxysilane, and heptadecafluorodecyltrimethoxysilane.

13. The oil-in-water emulsified cosmetic composition according to claim 1, wherein the silane compound is present and is octyltriethoxysilane or octyltrimethoxysilane.

14. The oil-in-water emulsified cosmetic composition according to claim 1, wherein the silazane compound is present and is hexamethyldisilazane.

* * * * *